United States Patent [19]

DeHavilland

[11] Patent Number: 5,538,353
[45] Date of Patent: Jul. 23, 1996

[54] LIQUID APPLICATOR

[75] Inventor: Lesley M. DeHavilland, Olathe, Kans.

[73] Assignee: Medi-Flex Hospital Products, Inc., Overland Park, Kans.

[21] Appl. No.: 519,575

[22] Filed: Aug. 25, 1995

[51] Int. Cl.$^6$ ............ A61M 35/00; A47L 13/34
[52] U.S. Cl. ............ 401/132; 401/133; 401/135; 604/3
[58] Field of Search ............ 401/132, 133, 401/135, 134; 604/3

[56] References Cited

U.S. PATENT DOCUMENTS

| | | | |
|---|---|---|---|
| 1,332,985 | 3/1920 | Jarrett | 401/135 X |
| 3,366,112 | 1/1968 | Antonik | 604/306 |
| 3,466,131 | 9/1969 | Arcudi | 401/132 |
| 3,768,916 | 10/1973 | Avery | 401/132 |
| 3,774,609 | 11/1973 | Schwartzman | 604/3 |
| 4,183,684 | 1/1980 | Avery, Jr. | 401/133 |
| 4,475,835 | 10/1984 | Uerboom et al. | 401/132 |
| 4,784,506 | 11/1988 | Koreska et al. | 401/132 |
| 4,899,739 | 2/1990 | Konishi | 128/156 |
| 5,147,337 | 9/1992 | Plone | 604/306 |

FOREIGN PATENT DOCUMENTS 16547  11/1915  United Kingdom .................. 604/3

Primary Examiner—Steven A. Bratlie
Attorney, Agent, or Firm—Hovey, Williams, Timmons & Collins

[57] ABSTRACT

A liquid applicator for applying a desired liquid to a surface includes a closed vial formed of a fracturable material containing the desired liquid, a body having a pocket with an open side and a shape adapted to receive the vial, and a porous element sealed to the body and closing off the open side of the pocket so that liquid flows through the element when the vial is fractured. The body has a flange protruding from the pocket along the open side thereof and a wing-like gripping member projects from the flange. The gripping member is spaced from the pocket and supported for pivoting movement relative to the pocket by the flange. The body also has structure for fracturing the vial, the structure being interposed between the pocket and gripping member. Upon pivoting of the gripping member, the structure flexes the pocket inwardly to exert a fracturing force against the vial when the member is pivoted towards the pocket.

20 Claims, 1 Drawing Sheet

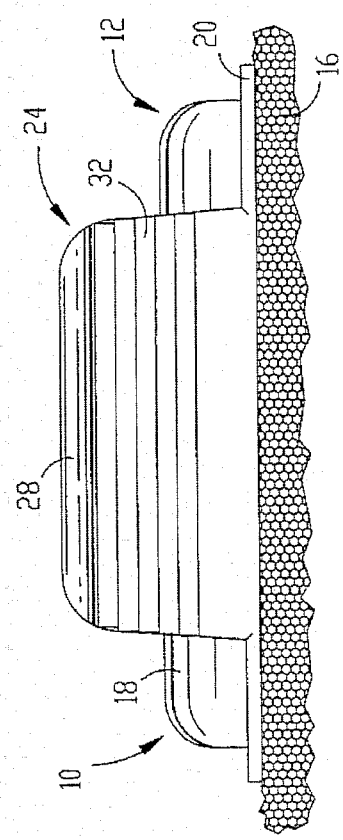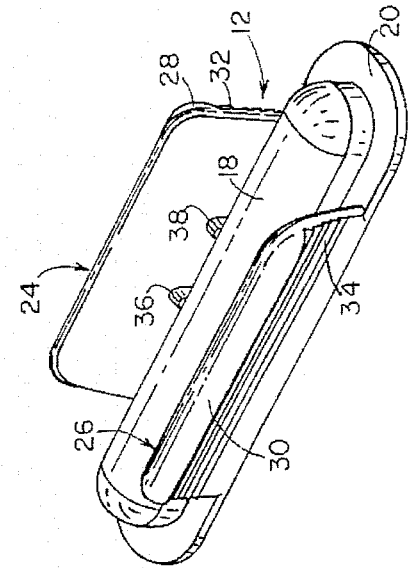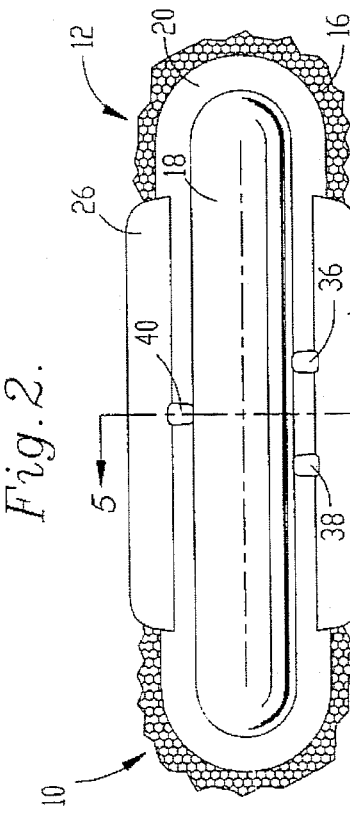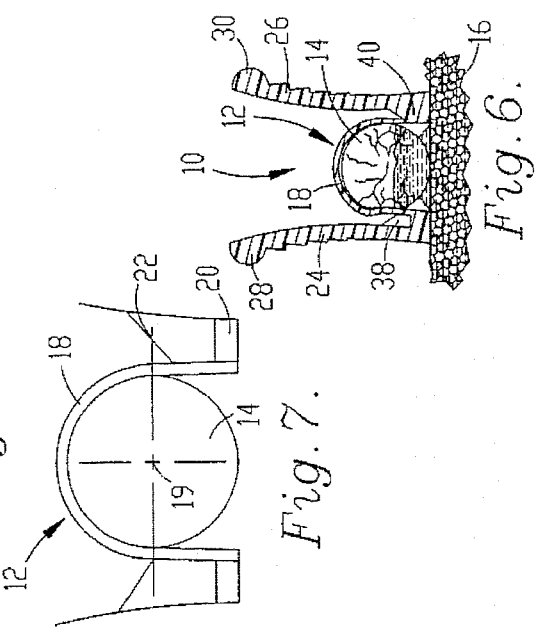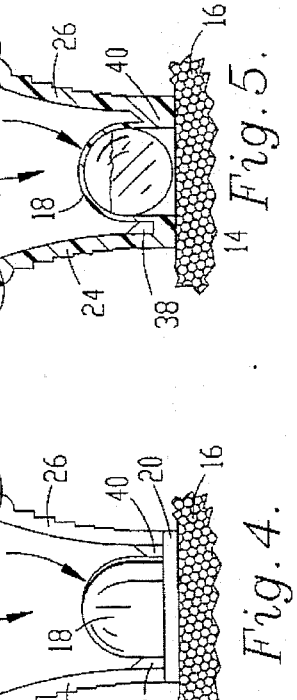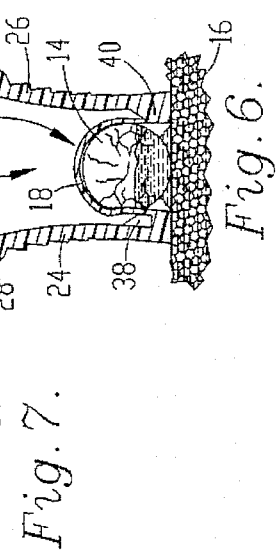

LIQUID APPLICATOR

BACKGROUND OF THE INVENTION

1. Field of the Invention

The present invention relates generally to a liquid application device and, more particularly, to a hand-held liquid applicator having a gripping member spaced from a pocket within which a liquid filled vial is received which may be squeezed by the user to fracture the vial, releasing the fluid from the vial so that it may be applied to a surface via a sponge.

2. Discussion of Prior Art

It is known to provide liquid applicators for applying liquids, such as medicaments or cleansing agents, wherein the applicator includes a body defining an open-sided cavity, a frangible vial retained within the cavity, and a sponge overlying the open side of the cavity over the vial. The liquid-filled vial is formed of glass and can take a variety of shapes. The body includes a shaped wall that conforms generally with the shape of the vial to define the open-sided cavity and a flange extending from the shaped wall along the open side of the cavity. In such applicators, the liquid-filled vial is fractured by the user grasping the shaped wall and exerting a squeezing force directly applied to the outer surface of the vial. Of course, the squeezing force necessary to fracture the vial depends on a number of factors such as the shape of the vial, the material of which the body or vial is formed, and the location at which the force is exerted.

One problem experienced in these conventional applicators is that shards or pieces of the fractured vial have a tendency to penetrate the shaped wall and injure the user's fingers. This can occur when the user over-exerts the squeezing pressure applied on the shaped wall. Further, the shaped wall is often difficult to grasp and hold onto when exerting the squeezing pressure or when applying the liquid to a surface, especially when the vial is spherical in shape or of a relatively small diameter, cylindrical configuration. Additionally, in such applicators, when the shaped wall is squeezed to fracture the vial, nothing prevents the vial from being pushed toward the open side of the cavity. Thus, the vial is able to move around within the pocket when the pocket is squeezed, inhibiting efficient fracturing of the vial. Moreover, such movement towards the open side of the cavity may also occur after the vial has been fractured, causing shards or pieces of the fractured vial to poke into or through the sponge. In situations wherein the applicator is being used to apply a liquid to the skin of a patient, shards of glass protruding into or through the sponge will obviously be detrimental.

Responsive to these problems, liquid applicators have been developed which include shaped walls having inward projections that engage the periphery of the vial to maintain the vial within the cavity and to prevent untoward movement of shards of the vial through the sponge when fracturing of the vial is effected. Further, applicators have been developed with shaped walls presenting a region to be grasped and squeezed by the user which provide a fulcruming effect so that the user squeezes the shaped wall at a location that is not directly in contact with the vial. In other words, the shaped wall is squeezed by the user pivoting the wall inwardly to engage the vial away from the region at which the wall is squeezed. However, the possibility still exists that a user will over-squeeze the shaped wall causing pieces of the fractured vial to shift to the region of squeezing and penetrate the wall. Although such liquid applicators represent an improvement over earlier conventional devices, there is a need to provide a liquid applicator that fully eliminates the risk of the user being injured by shards of the vial penetrating the shaped wall. Further, there is a need for a liquid applicator that has improved structure for gripping the applicator, while preventing untoward movement of the vial or pieces thereof toward the sponge.

OBJECTS AND SUMMARY OF THE INVENTION

Thus, it is an object of the present invention to provide an improved hand-held applicator having a body which may be squeezed to fracture the vial enclosed within the body, releasing the liquid contained in the vial so that the liquid may be applied by the sponge. Another object of the present invention is to provide an applicator which permits the user to squeeze the body at a location remote from the shaped wall defining the cavity.

It is another object of the present invention is to provide a member or members for gripping the applicator which are not limited to a shape conforming to the shape of the vial which enhance handling of the applicator while permitting the aforementioned remote squeezing. A further object of the present invention is to provide the body with structure that maintains the vial within the body and prevents untoward movement of the vial through the sponge when the body is squeezed to fracture the vial.

In accordance with these and other objects evident from the following description of a preferred embodiment of the invention, the liquid applicator includes a closed vial formed of a fracturable material containing a liquid to be applied, a body having a pocket with an open side and a shape adapted to receive the vial, and a porous element sealed to the body and closing off the open side of the pocket so that liquid flows through the element when the vial is fractured. The body also has a flange protruding from the pocket along the open side thereof and a wing-like gripping member projecting from the flange. The member is spaced from the pocket and supported for pivoting movement relative to the pocket by the flange. Finally, the body has structure for fracturing the vial interposed between the pocket and gripping member, which flexes the pocket inwardly to exert a fracturing force against the vial when the member is pivoted towards the pocket.

Preferably, the vial is elongated to define a central longitudinal axis, and the pocket is similarly shaped to define an axis that is generally collinear with the vial axis when the vial is received in the pocket and an axial plane that includes the pocket axis and is substantially parallel to the flange. Additionally, the body includes a pair of elongated gripping members running along the length of the pocket, which cause the inward movement of the pocket when the members are pivoted toward one another. The structure for fracturing the vial preferably includes a retaining tab positioned along the length of the pocket adjacent one gripping member, and a breaking tab also positioned along the length of the pocket but adjacent the other gripping member. Moreover, the retaining tab is configured to move the pocket inwardly at a location between the axial plane and flange such that the fracturing force effected by the retaining tab forces the vial away from the open side of the pocket.

By providing a liquid applicator in accordance with the present invention, numerous advantages are realized. For example, handling of the applicator is enhanced. Handling of the applicator is extremely important when it is employed as a cleansing agent dispenser in preparation for surgery wherein such use conditions are rigorous and slippery. Further, the member presents a squeezing location spaced from the pocket within which the vial is enclosed. Thus, if a shard or piece of a fractured vial penetrates the pocket, it is most unlikely that the user will be injured thereby.

The preferred pair of gripping members provide a lever action that gains mechanical advantage as the members are pivoted towards one another and concentrates the fracturing force on the vial, enhancing fracturing thereof. This mechanical advantage results from the provision of the retaining and breaking tabs which localize the pressure exerted on the relatively large gripping members, increasing the pressure exerted on the vial at the tabs. As a result of this localization of the fracturing pressure exerted by the user, the vial actually shatters with a distinct audible "pop" upon fracture, and the liquid contained in the vial saturates the porous element, eliminating the conventional practice of repeatedly squeezing the applicator to force liquid from the vial.

A further advantage of the inventive construction results from the use of the retaining tab, wherein shards of the fractured vial are directed away from the porous element during fracture.

BRIEF DESCRIPTION OF THE DRAWING FIGURES

A preferred embodiment of the invention is described in detail below with reference to the attached drawing figures, wherein:

FIG. 1 is a perspective view of a body element forming a part of a liquid applicator constructed in accordance with the preferred embodiment;

FIG. 2 is an enlarged side elevational view of the liquid applicator;

FIG. 3 is a top plan view of the applicator;

FIG. 4 is a front elevational view of the applicator;

FIG. 5 is a cross-sectional view taken along line 5—5 of FIG. 3;

FIG. 6 is a vertical cross-sectional view similar to FIG. 5, illustrating the gripping members sufficiently pivoted toward one another to fracture the vial; and FIG. 7 is a schematic cross-sectional view of the applicator, illustrating the general collinearity of the vial axis and pocket axis and configuration of the retaining and breaking tabs relative to such axes.

DETAILED DESCRIPTION OF THE PREFERRED EMBODIMENT

Turning initially to FIG. 5, the preferred embodiment contemplates a liquid applicator 10 generally including a body 12, a closed, liquid-filled vial 14 received in the body 12, and a porous element 16 secured to the body 12 and enclosing the vial 14 within the body 12 so that liquid flows through the element 16 when the vial 14 is fractured.

The vial 14 can be used for containing various liquids such as medicaments, cleansing agents, cosmetics, polishes or the like. In the illustrated embodiment, the vial 14 contains an antiseptic solution to be applied to a patient's skin (not shown) prior to surgery. Particularly, the solution includes silicon that is utilized to dry the patient's skin and serve as a partial adhesive for a tape-like sheet that is placed on the patient to facilitate suturing of the patient once surgery is completed. Although the vial 14 is illustrated as an elongated cylinder, it will be appreciated that the principles of the present invention may also be applied to spherical or elongated polygonal vials. Preferably, the vial 14 is formed of glass, although other materials are entirely within the scope of the present invention. The wall of the glass vial 14 is of a thickness sufficient to contain the desired liquid during transport and storage, yet allow the vial to be fractured upon the application of localized pressure.

As shown in FIG. 2, the body 12 is preferably formed of high density polyethylene although any material exhibiting similar flexibility and integrity may be used. The body 12 includes an open-sided pocket 18 within which the vial is received and a flange 20 protruding from the pocket 18 along the open side thereof. The pocket 18 has a shape generally conforming to the shape of the vial 14, as shown in FIG. 5. Accordingly, as shown in FIG. 7, the preferred pocket 18 is elongated and has a U-shaped side wall, which defines a pocket axis 19 that is generally collinear with the central longitudinal axis of the vial 14 and an axial plane 22 which includes the pocket axis and is generally parallel to the flange 20.

With reference to FIG. 1, the body also includes a pair of elongated gripping members 24, 26 projecting from the flange 20 and having a wing-like configuration. The members 24, 26 run along the length of the pocket and are each spaced from the pocket 18 on opposite sides thereof. Along the upper free edge of each of the members 24, 26, ribs 28, 30 jut laterally outward to facilitate handling of the applicator. Further, each of the members 24, 26 are provided with a relatively large, textured outer surface to prevent slippage from the user's hand during application, which in the illustrated embodiment takes the form of a series of steps 32, 34. As shown in FIG. 4, the flange 20 supports the gripping members 24, 26 for pivoting movement relative to the pocket 18. Accordingly, the gripping members 24, 26 may be grasped by the user and squeezed toward one another against the pocket, and this pivoting movement is accommodated by the flexing of the flange 20.

As shown in FIG. 3, the body also includes structure for fracturing the vial. Preferably, the structure includes a pair of breaking tabs 36, 38 and a retaining tab 40 interposed between the gripping members 24, 26 and the pocket 18. The breaking tabs 36, 38 interconnect the flange 20, the gripping member 24 and the pocket 18. Moreover, as shown in FIGS. 4–7, the breaking tabs 36, 38 each include an upper edge that angles inwardly and downwardly from the gripping member 24 to a location along the pocket 18 generally corresponding to the axial plane 22. Similarly, the retaining tab 40 interconnects the flange 20, the gripping member 26 and the pocket 18. However, the upper edge of the retaining tab 40 angles inwardly and downwardly from the gripping member 26 to a location along the pocket 18 below the axial plane 22 and above the flange 20.

As shown in FIG. 2, all of the tabs 36, 38, 40 have a very short length relative to the length of the gripping members 24, 26 so that when the gripping members 24,26 are pivoted toward one another by the user, the tabs 36,38,40 flex the pocket inwardly at positions immediately adjacent the tabs to exert radial forces against the vial. In other words, the textured outer surfaces of the gripping members 24, 26 present a gripping area which is significantly larger than the area of the tabs 36, 38, 40 which flex the pocket 18 inwardly, thereby localizing the forces effected by squeezing the members 24, 26 toward one another and enhancing fracturing of the vial. More particularly, the configuration of the breaking tabs 36, 38 causes the portion of the pocket extending from the axial plane 22 to the flange 20 to move inwardly at the tabs 36, 38. The inwardly moving pocket 18 engages the outermost point of the vial 14 to exert localized fracturing forces against the vial 14 that are generally vertically aligned with its central axis. The fracturing forces applied by the breaking tabs 36, 38 do not cause the vial 14 to move toward or away from the open side of the pocket 18. On the other hand, the retaining tab 40 causes a portion of the pocket 18 extending from the flange 20 to a location between the flange 20 and axial plane 22 to move inwardly in the region of the tab 40. The inwardly moving pocket 18 effected by the retaining tab 40 engages the vial 14 at a point offset beneath the axial plane 22, thereby exerting a localized fracturing force against the vial 14 which pushes the vial 14 away from the open side of the pocket 18. Thus, the configuration of the retaining tab 40 maintains the vial 14 within the pocket when the gripping members 24, 26 are pivoted toward one another to fracture the vial 14. The vial is maintained within the pocket 18 so that the vial does not shift prior to the localized fracturing forces being applied thereon and to prevent shards of a fractured vial from penetrating the porous element 16.

As best shown in FIG. 3, the retaining tab 40 is centrally disposed along the length of the pocket 18. Preferably, the breaking tabs 36, 38 are spaced axially from the retaining tab 40 and from one another on opposite sides of the tab 40. The relative positioning of the tabs 36, 38, 40 concentrates the fracturing forces in a somewhat triangular pattern, enhancing the fracturing of the vial 14. However, it will be appreciated that the principles of the present invention are equally applicable to various other structure for fracturing the vial 14, such as a retaining tab 40 and a single breaking tab.

The porous element 16 is secured to the body 12 over the open side of the pocket 18 and encloses the vial 14 within the pocket so that liquid flows from the pocket 18 and through the element 16 when the vial 14 is fractured. In the illustrated embodiment, the element 16 is adhesively secured to the flange 20 to prevent leakage between the flange 20 and element 16. However, it will be appreciated that the element may be attached to the flange 20 by other means such as stitching, heat sealing, or chemical bonding. Further, the preferred porous element 16 is cut from a sheet of sponge material having the desired porosity for the liquid to be dispensed, whereby liquid is prevented from flowing immediately through the element 16 when the vial 14 is fractured. In other words, once a vial 14 is fractured, the released liquid saturates the element 16 and flows from the element 16 only as the surface absorbs the liquid from the saturated element 16, causing the pocket 18 to essentially function as a reservoir of the desired liquid.

In use, the applicator 10 presents a hand-held liquid applicator that is squeezed to release the desired liquid contained therein for application to a surface. The applicator 10 is designed to be grasped by the user so that the gripping members 24, 26 are held between the thumb or palm and fingers of one hand of the user. The members 24, 26 preferably include the ribs 28, 30 and textured regions 32, 34 to facilitate handling of the applicator 10 and to inhibit slippage from the user's hand. The vial 14 is fractured by the user squeezing or pivoting the gripping members 24, 26 toward one another. The pivoting movement of the members 24, 26 is transferred by the tabs 36, 38, 40 to the pocket 18 to move the pocket 18 inwardly and exert discrete localized fracturing forces against the vial 14. The gripping members 24, 26 provide a lever action that gains mechanical advantage as the members 24, 26 are pivoted towards one another. Accordingly, if the user has limited gripping strength, or if the wall of the vial 14 is exceptionally thick, the members 24, 26 ensure fracturing of the vial 14. As shown in FIG. 6, once the members 24, 26 have been sufficiently pivoted, the resulting forces fracture the vial 14 releasing the liquid contained therein. Further, the retaining tab 40 forces the vial 14 away from the open side of the pocket 18 during fracturing which prevents shards of glass from penetrating the porous element 16. Once the vial 14 is fractured, liquid flows from the vial 14 to the pocket 18 and ultimately into the porous element 16. The saturated element 16 is then brought into contact with a surface to apply the liquid thereto.

Although the invention has been described with reference to the preferred embodiment illustrated in the attached drawing figures, it is understood that substitutions may be made and equivalents employed herein without departing from the scope of the invention as recited in the claims. Further, the inventors hereby state their intent to rely on the Doctrine of Equivalents to determine and assess the reasonably fair scope of their invention as pertains to any apparatus not materially departing from but outside the literal scope of the invention as set out in the following claims.

What is claimed is:

1. A liquid applicator comprising:

an elongated closed vial formed of a fracturable material containing a liquid to be applied, said vial presenting a central longitudinal axis;

a body including
an elongated pocket having an open side and a shape adapted to receive the vial, said pocket presenting an axis that is generally collinear with the vial axis when the vial is received in the pocket and an axial plane that includes the pocket axis and is substantially parallel to the open side thereof, a flange protruding from the pocket along the open side thereof, a pair of elongated, wing-like gripping members projecting from the flange and extending along the length of the pocket, the members being spaced from the pocket and supported for pivoting movement relative to the pocket by the flange, structure for fracturing the vial interposed between the pocket and gripping members, said structure flexing the pocket inwardly to exert a fracturing force against the vial when the members are pivoted toward one another; and a porous element secured to the body and closing off the open side of the pocket so that liquid flows through the element when the vial is fractured.

2. A liquid applicator as claimed in claim 1, wherein said gripping members each include a rib spaced from the flange and extending along the length thereof and a textured surface between the rib and flange, facilitating handling of the applicator.

3. A liquid applicator as claimed in claim 1, wherein said structure for fracturing the vial includes a retaining tab positioned along the length of the pocket adjacent one gripping member, said retaining tab being configured to move the pocket inwardly at a location between the axial plane and flange such that the fracturing force effected by the retaining tab forces the vial away from the open side of the pocket, and said structure further includes a breaking tab positioned along the length of the pocket adjacent the other gripping member and being configured to move the pocket inwardly generally at the axis of the pocket.

4. A liquid applicator as claimed in claim 3, wherein said retaining tab includes an engagement surface extending between said one gripping member and the pocket and intersecting the pocket at a location between the axial plane and flange, and said breaking tab includes an engagement surface extending between said other gripping member and the pocket and intersecting the pocket at a location aligned with the axial plane of the pocket.

5. A liquid applicator as claimed in claim 1, wherein said structure for fracturing the vial includes a retaining tab positioned along the length of the pocket adjacent one gripping member and a pair of spaced-apart breaking tabs adjacent the other gripping member, each of said breaking tabs being spaced axially from the retaining tab and one another along the length of the pocket.

6. A liquid applicator as claimed in claim 5, wherein said retaining tab is configured to move the pocket inwardly at a location between the axial plane and flange such that the fracturing force effected by the retaining tab forces the vial away from the open side of the pocket, and said breaking tabs are configured to move the pocket inwardly generally at the axial plane thereof.

7. A liquid applicator as claimed in claim 6, wherein said retaining tab extends obliquely from said one gripping member to the pocket at a location between the axial plane and flange and further extending along the pocket to the flange, interconnecting said one gripping member, the flange and the pocket, said breaking tabs extend obliquely from said other gripping member generally to the axial plane of the pocket and further extending along the pocket to the flange, interconnecting said other gripping member, the flange and the pocket.

8. A liquid applicator comprising:

a closed vial formed of a fracturable material containing a liquid to be applied;

a body including
  a pocket having an open side and a shape adapted to receive the vial,
  a flange protruding from the pocket along the open side thereof,
  a wing-like gripping member projecting from the flange, the member being spaced from the pocket and supported for pivoting movement relative to the pocket by the flange, said member presenting a gripping area upon which a squeezing force may be applied to pivot the member towards the pocket,
  structure for fracturing the vial interposed between the pocket and gripping member, said structure presenting a fracturing area that flexes the pocket inwardly to transfer the squeezing force to the vial when the member is pivoted towards the pocket, said fracturing area being less than said gripping area, localizing the squeezing force to enhance fracturing of the vial; and a porous element secured to the body and closing off the open side of the pocket so that liquid flows through the element when the vial is fractured.

9. A liquid applicator as claimed in claim 8, wherein said structure for fracturing the vial including a plurality tabs spaced apart along the pocket.

10. A liquid applicator as claimed in claim 9, wherein said vial is elongated and defines a central longitudinal axis, and said pocket is elongated to define an axis that is generally collinear with the vial axis when the vial is received in the pocket and an axial plane that includes the pocket axis and is substantially parallel to the flange.

11. A liquid applicator as claimed in claim 10, wherein said body includes a pair of elongated gripping members running along the length of the pocket, each of said members having at least one of the tabs adjacent thereto that flexes the pocket inwardly to transfer the squeezing force to the vial when the members are pivoted toward one another, said at least one of the tabs presents a length less than the length of the member adjacent thereto.

12. A liquid applicator as claimed in claim 11, wherein said gripping members each include a rib spaced from the flange and extending along the length thereof and a textured surface between the rib and flange, facilitating handling of the applicator.

13. A liquid applicator a claimed in claim 11, wherein said plurality of tabs include a retaining tab adjacent one gripping member and a breaking tab adjacent the other gripping member.

14. A liquid applicator as claimed in claim 13, wherein said retaining tab is configured to move the pocket inwardly at a location between the axial plane and flange such that the squeezing force transferred thereby forces the vial away from the open side of the pocket.

15. A liquid applicator as claimed in claim 14, wherein said breaking tab is configured to move the pocket inwardly generally at the axis of the pocket.

16. A liquid applicator as claimed in claim 15, wherein said retaining tab includes an engagement surface extending between said one gripping member and the pocket and intersecting the pocket at a location between the axial plane and flange, and said breaking tab includes an engagement surface extending between said other gripping member and the pocket and intersecting the pocket at a location aligned with the axial plane of the pocket.

17. A liquid applicator as claimed in claim 11, wherein said plurality of tabs include a retaining tab adjacent one gripping member and a pair of spaced-apart breaking tabs adjacent the other gripping member, each of said breaking tabs being spaced axially from the retaining tab.

18. A liquid applicator as claimed in claim 17, wherein said retaining tab is configured to move the pocket inwardly at a location between the axial plane and flange such that the squeezing force transferred thereby forces the vial away from the open side of the pocket.

19. A liquid applicator as claimed in claim 18, wherein said breaking tabs are configured to move the pocket inwardly generally at the axial plane thereof.

20. A liquid applicator as claimed in claim 19, wherein said retaining tab extends obliquely from said one gripping member to the pocket at a location between the axial plane and flange and further extending along the pocket to the flange, interconnecting said one gripping member, the flange and the pocket, said breaking tabs extend obliquely from said other gripping member generally to the axial plane of the pocket and further extending along the pocket to the flange, interconnecting said other gripping member, the flange and the pocket.

* * * * *